United States Patent
Funada et al.

(10) Patent No.: US 12,201,131 B2
(45) Date of Patent: *Jan. 21, 2025

(54) AQUATIC ORGANISM GROWTH PROMOTOR

(71) Applicant: Toray Industries, Inc., Tokyo (JP)

(72) Inventors: Shigeyuki Funada, Kamakura (JP); Hiroyuki Kurihara, Otsu (JP); Katsushige Yamada, Kamakura (JP)

(73) Assignee: Toray Industries, Inc., Tokyo (JP)

(*) Notice: Subject to any disclaimer, the term of this patent is extended or adjusted under 35 U.S.C. 154(b) by 1399 days.

This patent is subject to a terminal disclaimer.

(21) Appl. No.: 16/342,601

(22) PCT Filed: Oct. 26, 2017

(86) PCT No.: PCT/JP2017/038642
§ 371 (c)(1),
(2) Date: Apr. 17, 2019

(87) PCT Pub. No.: WO2018/079641
PCT Pub. Date: May 3, 2018

(65) Prior Publication Data
US 2019/0261653 A1    Aug. 29, 2019

(30) Foreign Application Priority Data

Oct. 27, 2016  (JP) ................. 2016-210701

(51) Int. Cl.
| | | |
|---|---|---|
| *A23K 50/80* | (2016.01) | |
| *A01K 61/59* | (2017.01) | |
| *A23K 10/37* | (2016.01) | |
| *A23K 20/111* | (2016.01) | |
| *A61K 31/09* | (2006.01) | |
| *A61K 36/899* | (2006.01) | |
| *A61P 43/00* | (2006.01) | |

(52) U.S. Cl.
CPC .............. *A23K 50/80* (2016.05); *A01K 61/59* (2017.01); *A23K 10/37* (2016.05); *A23K 20/111* (2016.05); *A61K 31/09* (2013.01); *A61K 36/899* (2013.01); *A61P 43/00* (2018.01); *Y02A 40/818* (2018.01); *Y02P 60/87* (2015.11)

(58) Field of Classification Search
CPC ...... A23K 10/37; A23K 20/111; A01K 61/59; A61K 36/899; A04K 61/59
See application file for complete search history.

(56) References Cited

U.S. PATENT DOCUMENTS

| | | | |
|---|---|---|---|
| 11,091,698 B2 * | 8/2021 | Funada | .................. C09K 17/50 |
| 2012/0034344 A1 | 2/2012 | Menon et al. | |
| 2013/0337030 A1 | 12/2013 | Adam et al. | |
| 2015/0353974 A1 | 12/2015 | Medoff | |

FOREIGN PATENT DOCUMENTS

| | | |
|---|---|---|
| JP | H07-231752 A | 9/1995 |
| JP | 2006-174779 | 7/2006 |
| JP | 2007-231752 | 9/2007 |
| JP | 2016-174588 | 10/2016 |

OTHER PUBLICATIONS

Mousavioun, P. and Doherty, W.O.S., "Chemical and thermal properties of fractionated bagasse soda lignin," Industrial Crops and Products, 31 (2010) 52-58 (Year: 2010).*

Bao, H. N. D. et al., "Preventing Discoloration and Lipid Oxidation in Dark Muscle of Yellowtail by Feeding an Extract Prepared from Mushroom (*Flammulina velutipes*) Cultured Medium," Aquaculture, Oct. 2009, vol. 295, Issues 3-4, pp. 243-249 (Abstract only—2 pages).

Fukada, H. et al., "Effects of Yuzu (*Citrus juntos*) Peel from Waste as an Aquaculture Feed Supplement on Growth, Environmental Load, and Dark Muscle Discoloration in Yellowtail *Seriola quinqueradiata*," Journal of Aquatic Food Product Technology, May 2013, vol. 23, issue 5, pp. 511-521 (Abstract only—2 pages).

Tolbert, A. et al., "Characterization and Analysis of the Molecular Weight of Lignin for Biorefining Studies," Biofuels Bioproducts & Biorefining, Jun. 2014, vol. 8, issue 6, pp. 836-856 (Abstract only—2 pages).

The Extended European Search Report dated May 29, 2020, of counterpart European Application No. 17864412.6.

Communication Pursuant to Article 94(3) EPC dated Nov. 15, 2023, of counterpart European Application No. 17864412.6.

E. Sugumaran et al., "Effect of Sugarcane Bagasse and Supplemental feed on Length and Weight of the catfish *Clarias batrachus* (Linn.)," International Journal of Fisheries and Aquatic Studies, 1(4), pp. 8-11, 2014.

* cited by examiner

*Primary Examiner* — Jeffrey P Mornhinweg
(74) *Attorney, Agent, or Firm* — DLA Piper LLP (US)

(57) ABSTRACT

An aquatic organism growth promotor, containing, as an effective ingredient, a low molecular weight lignin having a molecular weight peak in a molecular weight range of 4,000 to 9,500 and/or a high molecular weight lignin having a molecular weight peak in a molecular weight range of 10,000 to 40,000, wherein the molecular weight peak is measured at a wavelength of 254 nm by GPC molecular weight analysis using an UV detector.

14 Claims, 6 Drawing Sheets

AQUATIC ORGANISM GROWTH PROMOTOR

TECHNICAL FIELD

This disclosure relates to agents that promote the growth of aquatic organisms and methods of promoting the growth of aquatic organisms using the same.

BACKGROUND

For feedstuffs for livestock, consideration is being given to effective utilization of plant resources that have conventionally been disposed of and, for example, removing lignins from wood biomass allows the wood biomass to be effectively utilized as feedstuffs for livestock (JP 07-231752 A). Consideration is also being given to adding various plant resources-derived chemical substances to feedstuffs to thereby enhance meat quality and growth of aquatic organisms. For example, it has been known for a long time that adding vitamin E or vitamin C to feedstuffs for fish has the effect of suppressing the browning and lipid oxidation of fish meat. Recently, it has been made clear that a similar effect can be obtained by using a waste *Flammulina velutipes* bed extract (Huynh N. D. Bao et al., *Aquaculture* 295, 243-249 (2009)) or the rind of a yuzu citrus fruit (*Journal of Aquatic Food Product Technology* 23, 5, 511-521 (2014)).

SUMMARY

We found out that a low molecular weight lignin having a molecular weight peak in a molecular weight range of 4,000 to 9,500 and/or a high molecular weight lignin having a molecular weight peak in a molecular weight range of 10,000 to 40,000 promote(s) the growth of aquatic organisms, wherein the molecular weight peak is measured at a wavelength of 254 nm by GPC molecular weight analysis using an UV detector.

We thus provide:
[1] An aquatic organism growth promotor containing, as an effective ingredient, a low molecular weight lignin having a molecular weight peak in a molecular weight range of 4,000 to 9,500 and/or a high molecular weight lignin having a molecular weight peak in a molecular weight range of 10,000 to 40,000, wherein the molecular weight peak is measured at a wavelength of 254 nm by GPC molecular weight analysis using an UV detector.
[2] The aquatic organism growth promotor according to [1], wherein the low molecular weight lignin and/or the high molecular weight lignin are/is derived from a bagasse alkaline hot-water extract.
[3] The aquatic organism growth promotor according to [1] or [2], which promotes the ecdysis of a crustacean.
[4] An aquatic organism growth promotion feedstuff, containing the aquatic organism growth promotor.
[5] The aquatic organism growth promotion feedstuff according to [4], containing the low molecular weight lignin and/or the high molecular weight lignin, wherein the lignin(s) content as a polyphenol amount is 0.007 wt % or more in terms of catechin.
[6] A method of promoting aquatic organism growth, including administering the aquatic organism growth promotor to an aquatic organism.
[7] A method of promoting aquatic organism growth, including feeding the aquatic organism growth promotion feedstuff to an aquatic organism.
[8] The method of promoting aquatic organism growth according to [6] or [7], wherein the aquatic organism is a crustacean.

A bagasse alkaline extract that has not been effectively utilized as a feedstuff for aquatic organisms used as an effective ingredient, and has an aquatic organism growth promotion effect.

DETAILED DESCRIPTION

Figure 1:
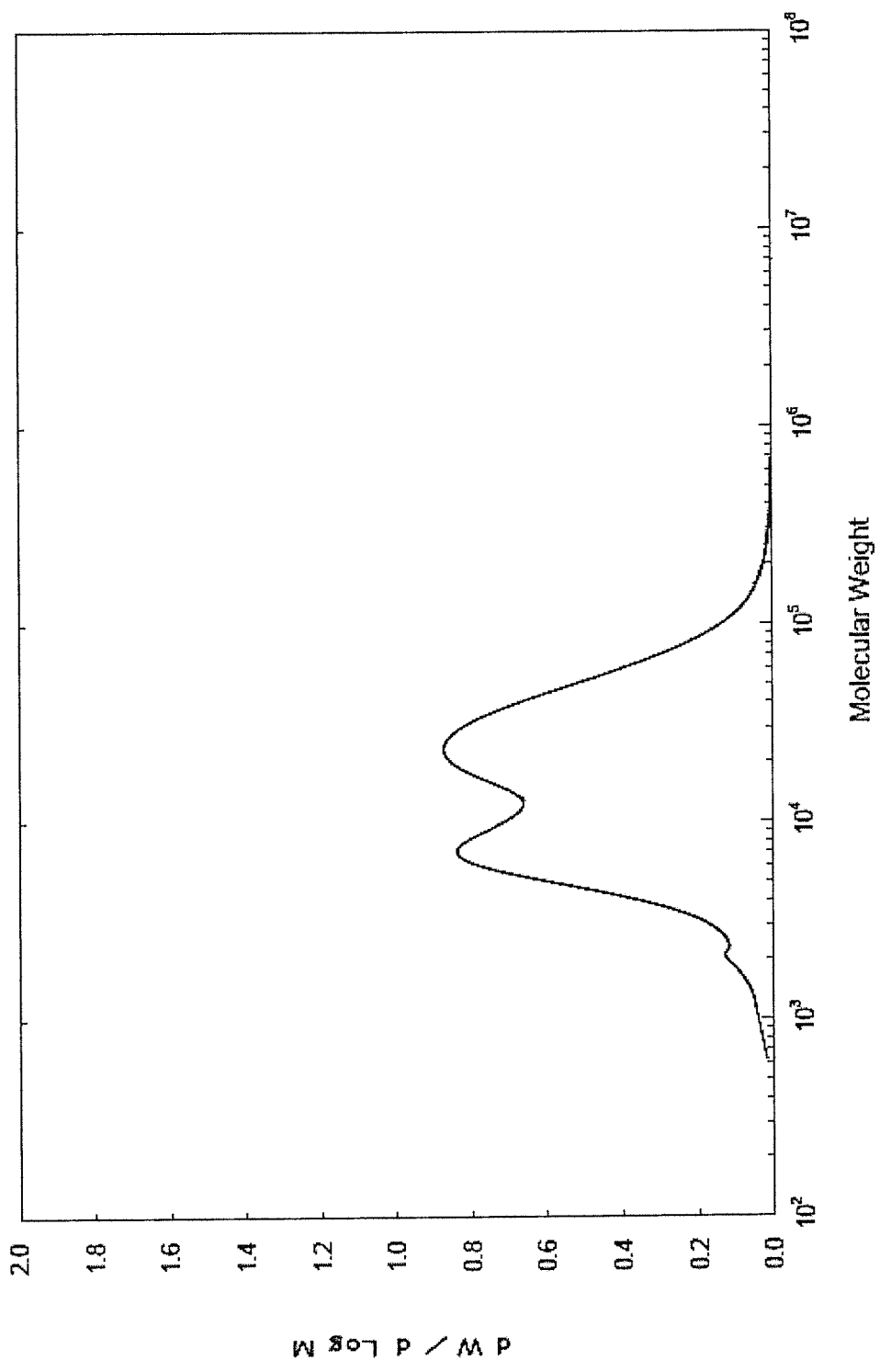
FIG. 1 shows a specific example of the GPC molecular weight analysis result of a bagasse alkaline hot-water extract.

Examples of our promotor will be described in detail.
Lignins are high molecular weight phenolic compounds derived from plants. Lignins have complicated and various structures, the details of which have not been clarified. In addition, although the molecular weights of lignins vary with the type of biomass, the extraction method, and the analysis method, the general number average molecular weights that have been reported are 2400 to 9700 (Biofuels Bioproducts & Biorefinering, Volume 8, Issue 6, 836-856 (2014)).

Our aquatic organism growth promotor contains, as an effective ingredient, a low molecular weight lignin having a molecular weight peak in a molecular weight range of 4,000 to 9,500 and/or a high molecular weight lignin having a molecular weight peak in a molecular weight range of 10,000 to 40,000, wherein the molecular weight peak is measured at a wavelength of 254 nm by GPC molecular weight analysis.

The low molecular weight lignin has a molecular weight peak in a molecular weight range of preferably 4,500 to 9,400, more preferably 5,000 to 9,300.

The high molecular weight lignin has a molecular weight peak in a molecular weight range of preferably 10,200 to 37,000, more preferably 11,000 to 35,000.

In addition, the molecular weight of a lignin can be judged based on the number average molecular weight. The low molecular weight lignin has an average molecular weight of preferably 3,500 to 6,000, more preferably 3,600 to 5,000, wherein the average molecular weight is a number average molecular weight measured by GPC molecular weight analysis using an UV detector. The high molecular weight lignin has an average molecular weight of preferably 10,000 to 20,000, more preferably 10,000 to 15,000, wherein the average molecular weight is a number average molecular weight measured by GPC molecular weight analysis using an UV detector. The lignin containing both a low molecular weight lignin and a high molecular weight lignin has a number average molecular weight of preferably 4,000 to 15,000, more preferably 6,000 to 10,000, wherein the average molecular weight is a number average molecular weight measured by GPC molecular weight analysis using an UV detector.

In addition, the low molecular weight lignin and the high molecular weight lignin may have a plurality of molecular weight peaks as long as the peaks are in the above-mentioned molecular weight ranges. Furthermore, the lignins may have a molecular weight peak outside the above-mentioned molecular weight ranges and, in this example, it is preferable that the highest peak of the molecular weight peaks at a wavelength of 254 nm is in a molecular weight range of 4,000 to 9,500 for the low molecular weight lignin and in a molecular weight range of 10,000 to 40,000 for the high molecular weight lignin.

Figure 2:
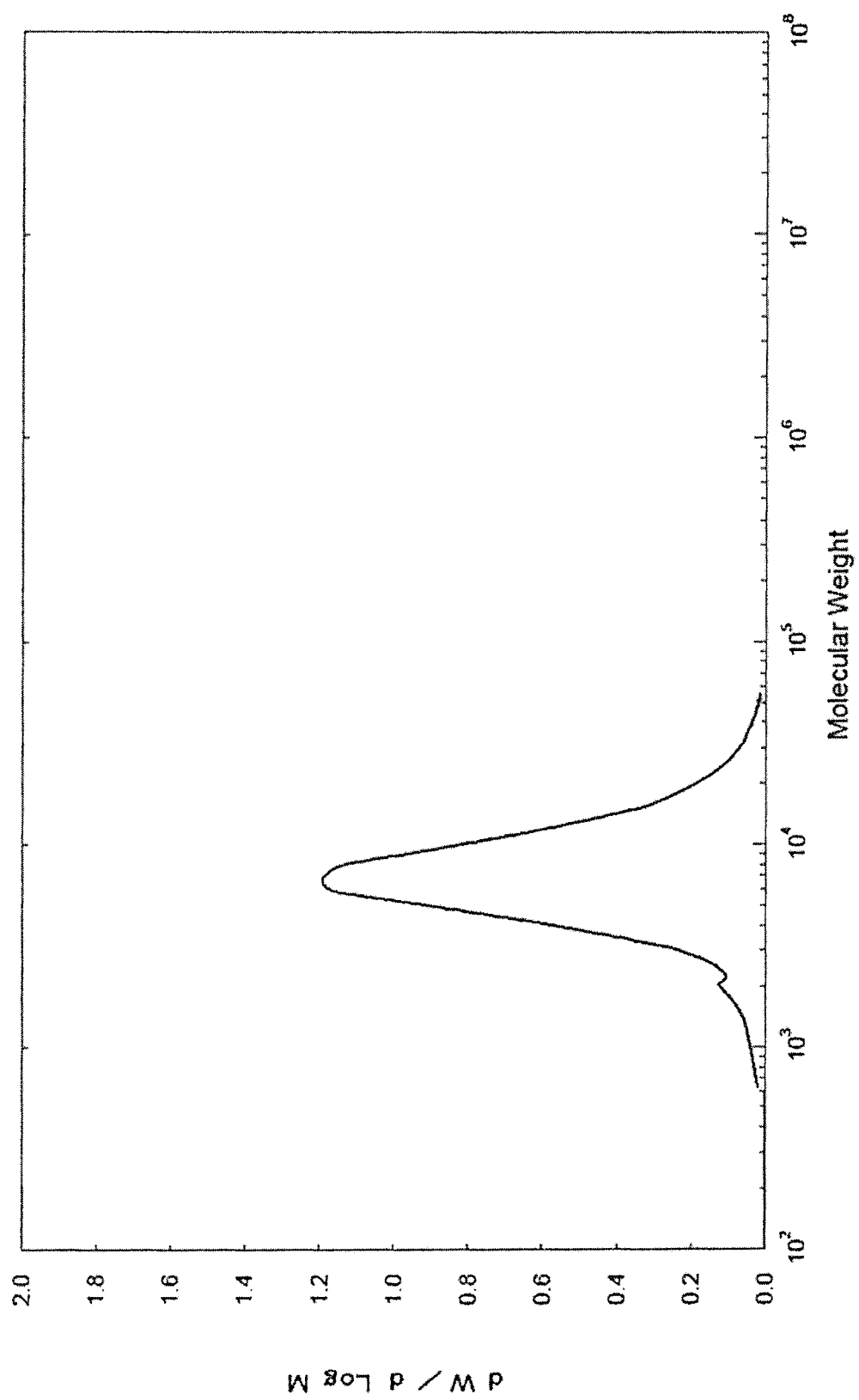
FIG. 2 shows a specific example of the GPC molecular weight analysis result of a low molecular weight lignin.
Figure 3:
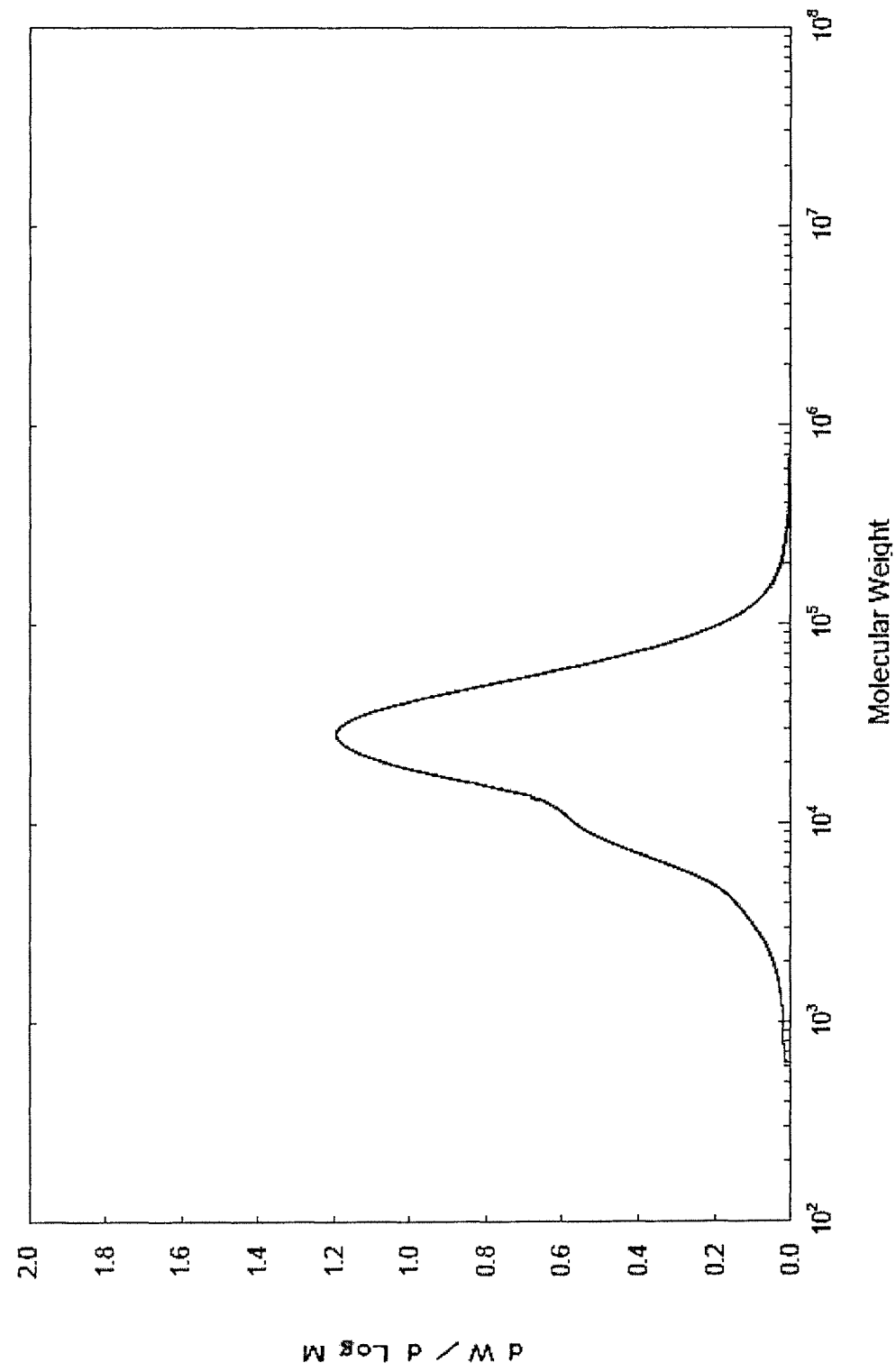
FIG. 3 shows a specific example of the GPC molecular weight analysis result of a high molecular weight lignin.

FIG. 1 shows a specific example of a GPC molecular weight analysis performed using an UV detector on a lignin containing both a low molecular weight lignin and a high molecular weight lignin. In addition, FIG. 2 shows a specific example of a low molecular weight lignin, and FIG. 3 shows a specific example of a high molecular weight lignin.

Hereinafter in the DESCRIPTION, our low molecular weight lignin is referred to as the "low molecular weight lignin," and our high molecular weight lignin is referred to as the "high molecular weight lignin."

GPC is an abbreviation of Gel Permeation chromatography, and enables compounds in a measurement sample to be separated in accordance with the molecular size. In addition, detecting the relative amounts of the separated polymers using a detector enables the molecular weights to be calculated. In a GPC molecular weight analysis, a standard polymer is used to preliminarily determine the relationship between the elution time and the molecular weight, on the basis of which relationship, the molecular weight of a measurement sample is calculated. The molecular weights of the low molecular weight lignin and the high molecular weight lignin are values measured using polyethylene glycol and polyethylene oxide as standard polymers.

As a detector for GPC molecular weight analysis, a detector capable of detecting the absorption wavelength region of lignin ranging from 250 to 300 nm can be used. Values measured at 254 nm at which cinnamic acids have no absorption were used in a GPC molecular weight analysis to eliminate the impact of cinnamic acids such as a coumaric acid and a ferulic acid that are low molecular weight aromatics. Values for the low molecular weight lignin and the high molecular weight lignin were detected using a multiple wavelength ultraviolet-visible absorption detector (SPD-M20A) made by Shimadzu Corporation. In GPC molecular weight analysis, number average molecular weights can be calculated using Equation (1).

$$Mn=\Sigma(Mi \cdot Ni)/\Sigma(Ni)=\Sigma Ci/\Sigma(Ci/Mi) \quad (1)$$

Mn represents a number average molecular weight, M represents a molecular weight, N represents the number of polymers, and C represents a sample concentration.

A column to be used for GPC molecular weight analysis is not limited to a particular one, and TSKgelGMPWXL and G2500PWXL were used to measure molecular weight values.

Examples of plants that can be used as raw materials for the low molecular weight lignin and/or the high molecular weight lignin include: conifers such as pine, cedar, and cypress; broadleaf trees such as eucalyptus and acacia; herbaceous biomass such as bagasse that is the sugar cane residual left after the juice is extracted, switchgrass, napier grasses, erianthus, corn stover, rice straw, and wheat straw; biomass derived from the aquatic environment such as algae and sea grasses; cereal hull biomass such as corn hulls, wheat hulls, soya bean hulls, and chaff; and the like. Bagasse is preferable.

Examples of methods of extracting the low molecular weight lignin and/or the high molecular weight lignin from the plants include extraction with an organic solvent (ethanol, ethyl acetate or the like), acid extraction, alkaline extraction, hydrothermal extraction, alkaline hydrothermal extraction, alkaline hot-water extraction and the like. Alkaline extraction or alkaline hot-water extraction is preferable, and alkaline hot-water extraction is more preferable.

Examples of alkaline compounds to be used for alkaline extraction, alkaline hydrothermal extraction, or alkaline hot-water extraction include, but are not particularly limited to, sodium hydroxide, potassium hydroxide, calcium hydroxide, magnesium hydroxide, ammonia, and the like. Sodium hydroxide or potassium hydroxide is preferable, and sodium hydroxide is more preferable.

For alkaline hot-water extraction, reaction conditions are preferably a pH of 10 to 13.5, a temperature of 80° C. to 120° C., and a processing time of 0.5 hours or more, more preferably a pH of 10.5 to 13.0, a temperature of 90° C. to 120° C., and a processing time of one hour or more. The upper limit of the alkaline concentration is not limited to a particular one as long as the concentration enables the low molecular weight lignin and the high molecular weight lignin to be obtained. An alkaline concentration that is too high to biomass affects the pH of the feedstuff to be added finally, and entails changes in the feedstuff preference that aquatic organisms have and in the growing environment for aquatic organisms. Accordingly the alkaline concentration is preferably 4 (wt/wt) % or less.

A hydrothermal treatment is a method of extracting lignin by treatment with pressurized hot-water (180 to 240° C.).

An alkaline hydrothermal extraction is a method of extracting lignin by treatment with pressurized hot-water (180 to 240° C.) under a pH condition of alkaline hot-water extraction.

Specific examples of alkaline hot-water extraction methods include a method in which the low molecular weight lignin and/or the high molecular weight lignin can be extracted by allowing a solution having a bagasse concentration of 5 (wt/wt) % (dry weight) to react with a 0.45 (wt/wt) % sodium hydroxide aqueous solution at 90° C. for two hours. The dry weight is a weight obtained after the bagasse is dried at 105° C. until the bagasse has a constant weight.

When it is desired to separate the low molecular weight lignin from the high molecular weight lignin, allowing the lignin mixture to be neutralized to pH 5 or less and undergo solid-liquid separation can separate the low molecular weight lignin as a liquid fraction from the high molecular weight lignin as a solid fraction. This is because it is characteristic of the low molecular weight lignin to dissolve in water under a pH 5 or less condition and it is characteristic of the high molecular weight lignin to deposit in water without dissolving. The high molecular weight lignin insolubilized under a pH 5 or less condition can then be dissolved in water at a pH made more alkaline than pH 5, for example, pH 8 or more.

A mode of administering the aquatic organism growth promotor to aquatic organisms may be a mode in which an effective amount of the low molecular weight lignin and/or the high molecular weight lignin is administered as a pharmaceutical to aquatic organisms, or may be a mode in which a feedstuff having a blend of the low molecular weight lignin and/or the high molecular weight lignin is fed as an aquatic organism growth promotion feedstuff. The mode of the aquatic organism growth promotion feedstuff is preferable.

Where the promotor is an aquatic organism growth promotion feedstuff, the amount of the low molecular weight lignin and/or the high molecular weight lignin contained in the foodstuff is preferably 0.007 wt % or more, more preferably 0.0128 wt % or more, still more preferably 0.14 wt % or more, as a polyphenol amount in terms of catechin. The upper limit of the polyphenol amount is not limited to a particular one as long as the amount allows the growth promotion effect to be achieved, and the amount is preferably 0.5 wt % or less, with which a relative reduction in the ratio of other feedstuff ingredients hardly makes an impact.

The polyphenol amount in terms of catechin is a value calculated using the Folin-Chiocalteu method. The Folin-Chiocalteu method was originally developed to analyze aromatic amino acids such as tyrosine and tryptophan, and proteins having these. It is a method in which a phenolic hydroxyl group, which is alkaline, reduces phosphotungstic acid or molybdic acid, and the generated blue color is quantitated by colorimetry at 700 to 770 nm. The same operation can be carried out using a specific reference material such as gallic acid or catechin, and quantitative values can be indicated in terms of the compound.

Where the aquatic organism growth promotor containing the low molecular weight lignin and/or high molecular weight lignin as an effective ingredient or a feedstuff containing the aquatic organism growth promotor is furnished to aquatic organisms, the growth of the aquatic organisms is more promoted, compared to when an aquatic organism feedstuff not containing the effective ingredient is furnished. The growth promotion mentioned here refers to an increase in the body weight (the weight of a fish containing moisture in its organism and yet to be cooked) and/or the body length of an aquatic organism, an increase in the number of times that crustaceans and the like undergo ecdysis, or a decrease in the death rate under congested aquiculture conditions (an increase in the survival rate).

A method of preparing the aquatic organism growth promotion feedstuff may be a method in which a liquid containing the effective ingredient is sprayed onto a common aquatic organism feedstuff or added to various feedstuff raw materials together with a binder such as water when the raw materials are blended. It is also possible that the effective ingredient is produced as a solid product by concentrating or drying a liquid containing the effective ingredient, or by adjusting the high molecular weight lignin to pH 5 or less and allowing the lignin to deposit in the liquid as above-mentioned, and then that the solid product can be mixed into a common aquatic organism feedstuff and furnished. In addition, when the effective ingredient is sprayed onto or mixed into a common aquatic organism feedstuff, the surface of the feedstuff may be coated with a hydrophobic substance or the like to allow the effective ingredient to be sufficiently retained in the feedstuff. Examples of hydrophobic substances to be used to coat include vegetable oil containing fatty acid, salad oil obtained by refining vegetable oil, animal oil and the like.

A feedstuff raw material other than an aquatic growth promotor contained in the aquatic organism growth promotion feedstuff is not limited to a particular one as long as the material can be used for the feedstuff, and examples of feedstuff raw materials include fish meal, Euphausiacea meal, squid meal, shrimp meal, Copepoda powder, starch, fish and shellfish extract, lecithin, yeast for feedstuff, yeast extract, calcium phosphate, refined fish oil, natural betaine, powdered glycyrrhiza, *Theragra chalcogramma* liver oil, various vitamins, and the like. The analytical composition of a feedstuff is not limited to a particular one as long as the composition contains crude protein, crude fat, crude fiber, crude ash, calcium, phosphorus and the like sufficiently to cause no notable problem in growing aquatic organisms.

In addition, the composition may contain a plant-derived substance as a substance other than the effective ingredient. Examples of substances other than the effective ingredient include cinnamic acids such as a coumaric acid and a ferulic acid, which are derived from plants. The concentration at which the other ingredient is contained in the feedstuff is preferably 0 to 0.02 wt % for a coumaric acid and 0 to 0.01 wt % for a ferulic acid, more preferably 0.0001 to 0.01 wt % for a coumaric acid and 0.00001 to 0.01 wt % for a ferulic acid, in that adding the ingredient at a higher concentration is costly. These coumaric acid and ferulic acid may be refined ones or crude extracts.

In addition, the feedstuff may contain an antioxidant for the purpose of oxidation prevention during storage of the feedstuff. Specific examples include ethoxyquin, dibutylhydroxytoluene, butylhydroxyanisole and the like.

A method of feeding feedstuffs to aquatic organisms is not limited to a particular one as long as the method follows a feeding timing and a feeding amount based on a conventional method, and the method is preferably, for example, such that feedstuffs can be furnished once a day to once a week, and that a feedstuff corresponding to preferably 2 to 5 wt % of the body weight of an aquatic organism is furnished one to three times a day in a manner adjusted to the remaining feeding amount.

An aquatic organism that is a subject of growth promotion is not limited to a particular one as long as the organism is one which lives in sea water or fresh water, and the organism is preferably a fish or a crustacean, more preferably a crustacean.

Specific examples of fishes include: Perciformes such as *Amphiprion ocellaris, Lateolabrax japonicus, Chromis notata, Thunnus*, and *Katsuwonus pelamis*; Anguilliformes such as *Anguilla*; Acipenseriformes such as Acipenseridae; Clupeiformes such as *Clupea pallasii* and *Sardinops melanostictus*; Cypriniformes such as *Cyprinus carpio, Carassius*, and *Misgurnus anguillicaudatus*; Siluriformes such as *Silurus asotus*; Salmoniformes such as *Plecoglossus, Oncorhynchus keta*, and *Oncorhynchus mykiss*; Acanthopterygii such as Beryciformes; Gadiformes such as *Theragra chalcogramma*; Lophiiformes such as stingfishes and Lophiidae; Rajiformes such as *Dasyatis akajei*; Scorpaeniformes such as *Sebastiscus marmoratus* and *Chelidonichthys spinosus*; Pleuronectiformes such as Pleuronectidae and *Paralichthys olivaceus*; Tetraodontiformes such as *Stephanolepis* and Tetraodontidae. Perciformes is more preferable.

Specific examples of crustaceans include Bathysquillidae, Gonodactylidae, Odontodactylidae, Harpiosquillidae, Squillidae, Aristeidae, Solenoceridae, Penaeidae, Sicyoniidae, Sergestidae, Oplophoridae, Atyidae, Pasiphaeidae, Eugonatonotidae, Palaemonidae, Alpheidae, Hippolytidae, Pandalidae, Glyphocrangonidae, Crangonidae, Cainbaridae, Astacidae, Nephropidae, Thaurnastochelidae, Polychelidae, Palinuridae, Scyllaridae, Axiidae, Galatheoidae, Porcellanidae, Lithodidae, Potamonidae, Raninidae, Homolodromiidae, Dynomenidae, Latreilliidae, Homolidae, Dorippidae, Calappidae, Inachidae, Hymenosornatidae, Parthenopidae, Cancridae, Leucosiidae, Cheiragonidae, Corystidae, Portunidae, Geryonidae, Xanthidae, Goneplacidae, Ocypodidae, Grapsidae, Pinnotheridae, and the like. In particular, preferable examples among these are: *Panulirus japonicus* in Palinuridae; *Ibacus, Parribacus japonicus*, and *Scyllar-*

*ides squamosus* in Scyllaridae; *Penaeus monodon, Litopenaeus vannamei* (white tiger prawn), *Marsupenaeus japonicus, Metapenaeus joyneri, Metapenaeopsis barbata, Litopenaeus vannamei* (whiteleg shrimp), *Penaeus semisulcatus* in Penaeidae; *Sergia lucens* in Sergestidae; *Pandalus borealis* and *Pandalus nipponensis* in Pandalidae; and *Nephropus japonicus* in Nephropidae.

EXAMPLES

Below, our promotors will be described specifically.

Reference Example 1 GPC Molecular Weight Analysis

GPC molecular weight analyses were carried out under the following conditions.
Detector: multiple wavelength ultraviolet-visible absorption detector UV (SPD-M20A made by Shimadzu Corporation, at a wavelength of 254 nm)
Column: TSKgelGMPW$_{XL}$ and G2500PW$_{XL}$, one each (7.8 mm in diameter×30 cm, from Tosoh Corporation)
Solvent: ammonia buffer (pH 11)/methanol (1/1=v/v)
Flow Rate: 0.7 mL/min
Column Temperature: 23° C.
Injection Volume: 0.2 mL
Standard Sample: monodisperse polyethylene oxide and polyethylene glycol, made by Tosoh Corporation, made by Polymer Laboratories Ltd.

Using the standard sample, a relationship between elution time and logarithms of a molecular weight was obtained preliminarily, converted as a weight fraction per Log M (wherein M is a molecular weight), dW/d log M (wherein W is a weight), and plotted with logarithms of the molecular weight as the abscissa against the ordinate such that the peak area corresponded to 1, followed by using the plot for analysis.

Reference Example 2 Polyphenol Amount Measurement

A suitably diluted measurement sample in an amount of 1.0 mL, 1.0 mL of a phenol reagent solution (from Nacalai Tesque, Inc.), and 5 mL of water were added to a 25 mL graduated flask and left to stand at room temperature for five minutes, and, to the resulting mixture, 10 mL of a 7% sodium carbonate aqueous solution was added. To the resulting mixture, water was further added to make up 25 mL, and mixed, and the resulting mixture was left to stand at room temperature for two hours. Part of the reaction liquid was taken out, filtrated through a PTFE filter 0.45 μm in diameter, and measured for absorbance at 750 nm (the sample was suitably diluted such that the absorbance was 0.6 ABS or less). The measurement result was calculated in terms of catechin using a catechin reagent (from Sigma-Aldrich Co. LLC, having a purity of 98% or more) as a standard material.

Reference Example 3 Aromatic Compound Measurement

The concentration of an aromatic compound such as a coumaric acid or a ferulic acid was measured under the following conditions.
Instrument: Hitachi high performance liquid chromatogram, LaChrom Eite
Column: Synergi 2.5μ Hydro-RP100A 100×3.00 mm (Phenomenex)
Mobile Phase: 0.1% phosphoric acid:acetonitrile=93:7 to 5:95, gradient
Detector: Diode Array
Flow Rate: 0.6 mL/min
Temperature: 40° C.

Test Example 1 Ecdysis Promotion Effect on Penaeid Shrimp (the Low Molecular Weight Lignin and the High Molecular Weight Lignin)

Preparation of Feedstuff

Bagasse in an amount of 1 kg (purchased from Taito Nosan K.K., produced in Vietnam) at 5 wt % by dry weight was added to and mixed with a 0.45 wt % sodium hydroxide aqueous solution, the resulting mixture was allowed to react at 90° C. for two hours, and adjusted to pH 7 with 6 N hydrochloric acid, and then, the solid was separated through a sieve, and filtrated through an MF film (tradename: TREFIL HFS Type, made by Toray Industries, Inc.) to prepare a bagasse alkaline hot-water extract. This alkaline extract was subjected to GPC molecular weight analysis using the method described in Reference Example 1. The analysis result is as shown in FIG. 1 and confirms that the obtained extract contained the low molecular weight lignin having a peak at a molecular weight of 7,000 and the high molecular weight lignin having a molecular weight peak at a molecular weight of 21,000. In addition, the number average molecular weight was 8,900. Furthermore, the amount of polyphenol in this bagasse alkaline extract was 0.2 wt % in terms of catechin, as measured in accordance with Reference Example 2. In addition, measurement of a coumaric acid and a ferulic acid by the method described in Reference Example 3 showed 0.08 wt % of coumaric acid and 0.016 wt % of ferulic acid, and the polyphenol content of the liquid containing only a coumaric acid and a ferulic acid at the same respective concentrations was 0.072 wt % in terms of catechin. This fact revealed that the amount of the low molecular weight lignin and the high molecular weight lignin as a polyphenol amount was 0.128 wt % in terms of catechin. This bagasse alkaline hot-water extract (having a solid content of 2% and a polyphenol content of 10% in terms of catechin with respect to the solid content) was sprayed onto and mixed with a feed mixture (Nosan Jirushi feed mixture, H Penaeid Shrimp Super B, for raising Penaeid shrimp, made by Higashimaru Shoyu Co., Ltd.) at 0.2% on the basis of the weight of the solute and with respect to the dry weight of the feedstuff (the polyphenol content with respect to the dry weight of the feedstuff was 0.02% in terms of catechin, and the amount of the low molecular weight lignin and the high molecular weight lignin as a polyphenol amount was 0.0128 wt % in terms of catechin). Furthermore, the surface of the feedstuff was coated with oil (Nisshin Salad Oil made by The Nisshin OilliO Group, Ltd.) that corresponded to 1% of the weight of the feedstuff. The prepared feedstuff was used as a feedstuff containing the low molecular weight lignin and the high molecular weight lignin.

Evaluation of Growth Promotion Effect

The aquatic organism growth promotion effect of the feedstuff containing the low molecular weight lignin and the high molecular weight lignin was evaluated using 24 Penaeid shrimp having an average body weight of 14.1 g (at a standard deviation of 1.5) and an average full length of 143.1 mm (at a standard deviation of 6.0) in three water tanks, eight shrimp per water tank (12.5 shrimp/m$^2$). Bottom sand was spread on the bottom in each water tank, the natural filtered sea water was heated to 20 to 25° C., and the water exchange rate was 3.8 times/day. The light condition was set to 12-hour brightness and 12-hour darkness, and the feedstuff containing the low molecular weight lignin and the high molecular weight lignin was fed immediately after the light was turned off, once a day. A feeding amount in terms of the ratio of the feed weight to the body weight of the shrimp of 3% was measured at the start, and then the feeding amount was increased stepwise in accordance with the state of feed intake such that the ratio was 4% on Day 9 after the start of the test, and the ratio was 5% on Day 20 after the start of the test. The test was performed for 30 days, during which the total number of times that the 24 shrimp underwent ecdysis was measured. The results are shown in Table 1.

Test Example 2 Ecdysis Promotion Effect on Penaeid Shrimp (the Low Molecular Weight Lignin)

Preparation of Feedstuff

The bagasse alkaline hot-water extract prepared in Test Example 1 was neutralized to pH 5 with 6 N hydrochloric acid, followed by depositing the high molecular weight lignin according. Diatomaceous earth at 1% was added to and mixed with the liquid, the resulting mixture was subjected to solid-liquid separation using a filter press (Model YTO, made by Yabuta Kikai Co., Ltd.), and the low molecular weight lignin liquid and the high molecular weight lignin were separated into the filtrate side and the solid content side respectively. The obtained filtrate was adjusted to pH 7 with a 50% (wt/v) sodium hydroxide solution to obtain a low molecular weight lignin liquid. This low molecular weight lignin liquid was subjected to GPC molecular weight analysis using the method described in Reference Example 1. The result is as shown in FIG. 2 and confirms that the lignin liquid contained the low molecular weight lignin having a peak at a molecular weight of 7,000. In addition, the number average molecular weight determined from the GPC molecular weight analysis result was 4,000. Furthermore, the amount of polyphenol in this low molecular weight lignin liquid was 0.1% in terms of catechin, as measured in accordance with Reference Example 2. In addition, measurement of a coumaric acid and a ferulic acid by the method described in Reference Example 3 showed 0.06 wt % of coumaric acid and 0.012 wt % of ferulic acid, and the polyphenol content of the liquid containing only a coumaric acid and a ferulic acid at the same respective concentrations was 0.05 wt % in terms of catechin. This fact revealed that the low molecular weight lignin existed at 0.05 wt % in terms of catechin. This low molecular weight lignin liquid (having a solid content of 1.5% and a content of 7% in terms of catechin with respect to the solid content) was sprayed onto and mixed with a feed mixture (Nosan Jirushi feed mixture, H Penaeid Shrimp Super B, for raising Penaeid shrimp, made by Higashimaru Shoyu Co., Ltd.) at 0.2% on the basis of the weight of the solute and with respect to the dry weight of the feedstuff (0.014% in terms of catechin with respect to the dry weight of the feedstuff, and 0.007 wt % in terms of catechin as the amount of the low molecular weight lignin and as a polyphenol amount). Furthermore, the surface of the feedstuff was impregnated with oil (Nisshin Salad Oil made by The Nisshin OilliO Group, Ltd.) which corresponded to 1% of the weight of the feedstuff. The prepared feedstuff was used as a feedstuff containing the low molecular weight lignin.

Evaluation of Growth Promotion Effect

The evaluation was performed in the same manner as in Test Example 1 except that the feedstuff prepared in this Test Example was used. The results are shown in Table 1.

Test Example 3 Ecdysis Promotion Effect on Penaeid Shrimp (the High Molecular Weight Lignin)

Preparation of Feedstuff

The bagasse alkaline hot-water extract prepared in Test Example 1 was neutralized to pH 3 with 6 N hydrochloric acid, followed by depositing the high molecular weight lignin. As a filter aid, diatomaceous earth at 1% was added to and mixed with the liquid, the resulting mixture was subjected to solid-liquid separation using a filter press (Model YTO, made by Yabuta Kikai Co., Ltd.), and the high molecular weight lignin containing the diatomaceous earth as a solid was obtained. The high molecular weight lignin containing diatomaceous earth was dried to have a solid content of 85%. This high molecular weight lignin (having a polyphenol content of 7% in terms of catechin with respect to the solid content) was mixed with a feed mixture (Nosan Jirushi feed mixture, H Penaeid Shrimp Super B, for raising Penaeid shrimp, made by Higashimaru Shoyu Co., Ltd.) at 0.2% on the basis of the weight of the solute and with respect to the dry weight of the feedstuff (the polyphenol content with respect to the dry weight of the feedstuff was 0.014% in terms of catechin). Furthermore, the surface of the feedstuff was impregnated with oil (Nisshin Salad Oil made by The Nisshin OilliO Group, Ltd.) that corresponded to 1% of the weight of the feedstuff. The prepared feedstuff was used as a feedstuff containing the high molecular weight lignin.

In addition, the molecular weight cutoff of the high molecular weight lignin was measured, apart from the preparation of feedstuff. To an insoluble high molecular weight lignin containing diatomaceous earth, 50% (wt/v) of sodium hydroxide was added to adjust the pH to 12, followed by dissolving the high molecular weight lignin. This high molecular weight lignin liquid was adjusted to pH 7 with 6 N hydrochloric acid, and the resulting liquid was subjected to GPC molecular weight analysis using the method described in Reference Example 1. The result is shown in FIG. 3. This analysis result confirms that the obtained lignin was the high molecular weight lignin having a peak at a molecular weight of 21,000, not containing the low molecular weight lignin. In addition, the number average molecular weight determined from this analysis result was 13,800. The amount of polyphenol in the high molecular weight lignin liquid adjusted here was 0.1 wt % in terms of catechin, as measured in accordance with Reference Example 2. In addition, the liquid was measured for a coumaric acid and a ferulic acid by the method described in Reference Example 3, and neither coumaric acid nor ferulic acid was detected.

Evaluation of Growth Promotion Effect

The evaluation was performed in the same manner as in Test Example 1 except that the feedstuff prepared in this Test Example was used. The results are shown in Table 1.

Test Example 4 Ecdysis Promotion Effect on Penaeid Shrimp (Additive-Free)

Preparation of Feedstuff

The surface of a feed mixture (Nosan Jirushi feed mixture, H Penaeid Shrimp Super B, for raising Penaeid shrimp, made by Higashimaru Shoyu Co., Ltd.) was impregnated with oil (Nisshin Salad Oil made by The Nisshin OilliO Group, Ltd.) which corresponded to 1% of the weight of the feedstuff, to prepare an additive-free feedstuff.

Evaluation of Growth Promotion Effect

The evaluation was performed in the same manner as in Test Example 1 except that the additive-free feedstuff in this Test Example was used. The results are shown in Table 1.

Test Example 5 Ecdysis Promotion Effect on Penaeid Shrimp (Bagasse Hydrothermally-Processed Liquid)

Preparation of Feedstuff

Figure 4:
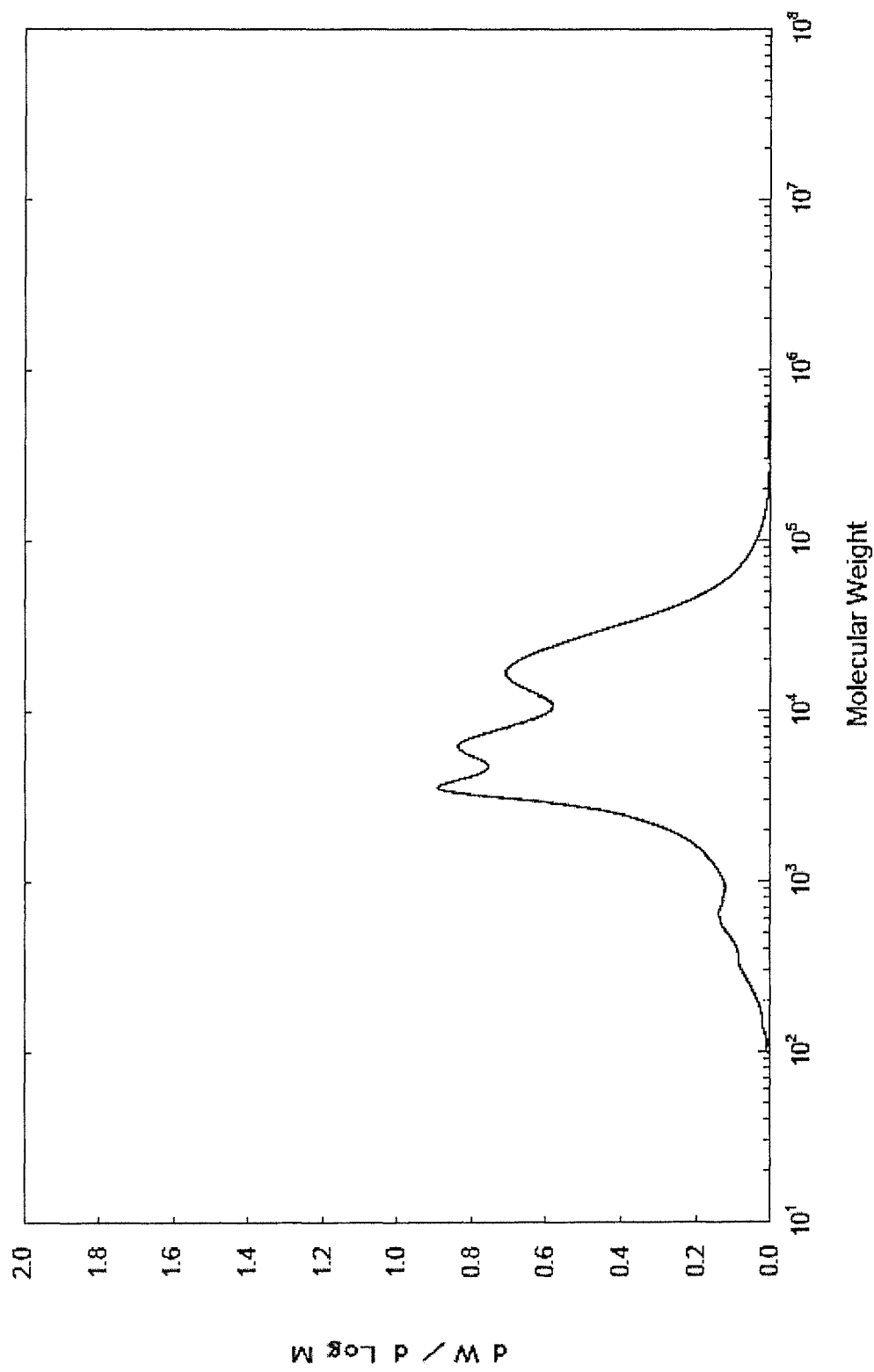
FIG. 4 shows a specific example of the GPC molecular weight analysis result of a bagasse hydrothermally-processed liquid.

Bagasse was adjusted to have a dry weight of 30%, and hydrothermally-processed (high pressure cooking-processed) under high pressure at 180° C. for ten minutes. The obtained bagasse hydrothermally-processed liquid was adjusted to pH 7 with 1 N sodium hydroxide. The bagasse hydrothermally-processed liquid was subjected to GPC molecular weight analysis using the method described in Reference Example 1, and the result is shown in FIG. 4. This analysis result has revealed that the bagasse hydrothermally-processed liquid contained lignins having a molecular weight peak at a molecular weight of 3,200, a molecular weight of 6,000, and a molecular weight of 17,000 in peak order from higher to lower. In addition, the number average molecular weight determined from the GPC molecular weight analysis result was 2,870. In the bagasse hydrothermally-processed liquid, the effective ingredient having the highest peak had the peak at a molecular weight of 4,000 or less. This effective ingredient having the highest peak was different from the low molecular weight lignin and the high molecular weight lignin, but the composition of the ingredient included the low molecular weight lignin and the high molecular weight lignin. In addition, the amount of polyphenol in this bagasse hydrothermally-processed liquid was 0.001% in terms of catechin (a solid content of 1.0%, and a content of 0.1% in terms of catechin with respect to the solid content), as measured in accordance with Reference Example 2. This bagasse hydrothermally-processed liquid was mixed with a feed mixture (Nosan Jirushi feed mixture, H Penaeid Shrimp Super B, for raising Penaeid shrimp, made by Higashimaru Shoyu Co., Ltd.) at 0.2% on the basis of the weight of the solute and with respect to the dry weight of the feedstuff (the polyphenol content with respect to the dry weight of the feedstuff was 0.0002% in terms of catechin). Furthermore, the surface of the feedstuff was impregnated with oil (Nisshin Salad Oil made by The Nisshin OilliO Group, Ltd.) that corresponded to 1% of the weight of the feedstuff.

Evaluation of Growth Promotion Effect

The evaluation was performed in the same manner as in Test Example 1 except that the feedstuff prepared in this Test Example was used. The results are shown in Table 1.

TABLE 1

| Ecdysis Promotion Effect on Penaeid Shrimp | |
|---|---|
| | Number of Times of Ecdysis |
| Test Example 1 (Low Molecular Weight Lignin and High Molecular Weight Lignin) | 27 |
| Test Example 2 (Low Molecular Weight Lignin) | 27 |
| Test Example 3 (High Molecular Weight Lignin) | 28 |

TABLE 1-continued

| Ecdysis Promotion Effect on Penaeid Shrimp | |
|---|---|
| | Number of Times of Ecdysis |
| Test Example 4 (Additive-free) | 24 |
| Test Example 5 (Bagasse Hydrothermally-processed Liquid) | 24 |

As shown in Table 1, the result revealed that the number of times that the Penaeid shrimp underwent ecdysis increased when the feedstuffs containing the low molecular weight lignin and/or the high molecular weight lignin in Test Examples 1 to 3 were used, compared when the additive-free feedstuff in Test Example 4 was used.

Test Example 6 Growth Promotion Effect on *Amphiprion ocellaris* (the Low Molecular Weight Lignin and the High Molecular Weight Lignin)

Preparation of Feedstuff

The bagasse alkaline hot-water extract prepared in Test Example 1 (having a solid content of 2% and a content of 10% in terms of catechin with respect to the solid content) was sprayed onto and mixed with a feed mixture (Ambrose 400 made by Feed One Co., Ltd.) at 0.2% on the basis of the weight of the solute and with respect to the dry weight of the feedstuff (0.02% in terms of catechin with respect to the dry weight of the feedstuff, and 0.0128 wt % in terms of catechin as the amount of the low molecular weight lignin and the high molecular weight lignin). Furthermore, the surface of the feedstuff was impregnated with oil (Nisshin Salad Oil made by The Nisshin OilliO Group, Ltd.) that corresponded to 1% of the weight of the feedstuff.

Evaluation of Growth Promotion Effect

The aquatic organism growth promotion effect of a feedstuff containing the low molecular weight lignin and the high molecular weight lignin was evaluated using *Amphiprion ocellaris* individuals having a body length of 20±3 mm in three water tanks, ten individuals per water tank (10 individuals/20 L). Natural filtered sea water was heated to about 25° C., and the water exchange rate was 50%/day. The light condition was set to 12-hour brightness and 12-hour darkness, and the feedstuff containing the low molecular weight lignin and the high molecular weight lignin was fed immediately after the light was turned off, once a day. The feeding amount was 3% with respect to the body weight of *Amphiprion ocellaris* measured at the start of the test. The test was performed for seven days, the *Amphiprion ocellaris* individuals were collected after the termination of the test, and the average body weight per individual was measured. The results are shown in Table 2.

Test Example 7 Growth Promotion Effect on *Amphiprion ocellaris* (the Low Molecular Weight Lignin)

Preparation of Feedstuff

The low molecular weight lignin liquid prepared in Test Example 2 (having a solid content of 1.5% and a content of 7% in terms of catechin with respect to the solid content) was sprayed onto and mixed with a feed mixture (Ambrose 400 made by Feed One Co., Ltd.) at 0.2% on the basis of the weight of the solute and with respect to the dry weight of the feedstuff (0.014% in terms of catechin with respect to the dry weight of the feedstuff, and 0.007 wt % in terms of catechin as the amount of the low molecular weight lignin and the high molecular weight lignin). Furthermore, the surface of the feedstuff was impregnated with oil (Nisshin Salad Oil made by The Nisshin OilliO Group, Ltd.) which corresponded to 1% of the weight of the feedstuff.

Evaluation of Growth Promotion Effect

The evaluation was performed in the same manner as in Test Example 6 except that the feedstuff containing the low molecular weight lignin liquid and prepared in this Test Example was used. The results are shown in Table 2.

Test Example 8 Growth Promotion Effect on Amphiprion ocellaris (the High Molecular Weight Lignin)

Preparation of Feedstuff

The insoluble high molecular weight lignin liquid prepared in Test Example 3 (having a solid content of 85% and a content of 7% in terms of catechin with respect to the solid content) was mixed with a feed mixture (Ambrose 400 made by Feed One Co., Ltd.) at 0.2% on the basis of the weight of the solute and with respect to the dry weight of the feedstuff (0.014% in terms of catechin with respect to the dry weight of the feedstuff). Furthermore, the surface of the feedstuff was impregnated with oil (Nisshin Salad Oil made by The Nisshin OilliO Group, Ltd.) that corresponded to 1% of the weight of the feedstuff.

Evaluation of Growth Promotion Effect

The evaluation was performed in the same manner as in Test Example 6 except that the feedstuff containing the high molecular weight lignin liquid and prepared in this Test Example was used. The results are shown in Table 2.

Test Example 9 Growth Promotion Effect on Amphiprion ocellaris (Additive-Free)

Preparation of Feedstuff

The surface of a feed mixture (Ambrose 400 made by Feed One Co., Ltd.) was impregnated with oil (Nisshin Salad Oil made by The Nisshin OilliO Group, Ltd.) that corresponded to 1% of the weight of the feedstuff, to prepare an additive-free feedstuff.

Evaluation of Growth Promotion Effect

The evaluation was performed in the same manner as in Test Example 6 except that the additive-free feedstuff in this Test Example was used. The results are shown in Table 2.

Test Example 10 Growth Promotion Effect on Amphiprion ocellaris (Bagasse Hydrothermally-Processed Liquid)

Preparation of Feedstuff

The bagasse hydrothermally-processed liquid prepared in Test Example 5 (having a solid content of 1% and a content of 0.1% in terms of catechin with respect to the solid content) was mixed with a feed mixture (Ambrose 400 made by Feed One Co., Ltd.) at 0.2% on the basis of the weight of the solute and with respect to the dry weight of the feedstuff (0.0002% in terms of catechin with respect to the dry weight of the feedstuff). Furthermore, the surface of the feedstuff was impregnated with oil (Nisshin Salad Oil made by The Nisshin OilliO Group, Ltd.) that corresponded to 1% of the weight of the feedstuff.

Evaluation of Growth Promotion Effect

The evaluation was performed in the same manner as in Test Example 6 except that the feedstuff containing the bagasse hydrothermally-processed liquid prepared in this Test Example was used. The results are shown in Table 2.

TABLE 2

| Growth Promotion Effect on *Amphiprion Ocellaris* | |
|---|---|
| | Average Body Weight (g) |
| Test Example 6 (Low Molecular Weight Lignin and High Molecular Weight Lignin) | 0.090 |
| Test Example 7 (Low Molecular Weight Lignin) | 0.090 |
| Test Example 8 (High Molecular Weight Lignin) | 0.092 |
| Test Example 9 (Additive-free) | 0.085 |
| Test Example 10 (Bagasse Hydrothermally-processed Liquid) | 0.084 |

As shown in Table 2, the result revealed that the average body weight of *Amphiprion ocellaris* individuals increased when the feedstuffs containing the low molecular weight lignin and/or the high molecular weight lignin in Test Examples 6 to 8 were used, compared when the additive-free feedstuff in Test Example 9 was used.

Test Example 11 Growth Promotion Effect on Penaeid Shrimp (the Low Molecular Weight Lignin and the High Molecular Weight Lignin)

Preparation of Feedstuff

The bagasse alkaline hot-water extract prepared in Test Example 1 (having a solid content of 2% and a content of 10% in terms of catechin with respect to the solid content) was sprayed onto and mixed with a feed mixture (Ebikaniconc made by Bio Science Co., Ltd.) during granulation, at 0.2% on the basis of the weight of the solute and with respect to the dry weight of the feedstuff (0.02% in terms of catechin with respect to the dry weight of the feedstuff, and 0.0128 wt % in terms of catechin as the amount of the low molecular weight lignin and the high molecular weight lignin). The prepared feedstuff was used as a feedstuff containing the low molecular weight lignin and the high molecular weight lignin.

Evaluation of Growth Promotion Effect

The aquatic organism growth promotion effect of a feedstuff containing the low molecular weight lignin and the high molecular weight lignin was evaluated using Penaeid shrimp having an average body weight of 32.2 mg (at a standard deviation of 11.3) and an average full length of 15.5 mm (at a standard deviation of 1.9), 150 shrimp per water tank (1,500 shrimp/m$^2$). With no bottom sand spread on the bottom in each water tank, natural filtered sea water was heated to 20 to 25° C., and the water exchange rate was 5 times/day. The light condition was set to 12-hour brightness and 12-hour darkness, and the feedstuff containing the low molecular weight lignin and the high molecular weight lignin was fed three times a day. With the feeding amount at 3 to 5% of the weight of the shrimp, the feeding amount was increased stepwise in accordance with the state of feed intake. The test was performed for 50 days, and the number of shrimp that survived, the average body weight, and the average full length for the period were measured. The results are shown in Table 3.

Test Example 12 Growth Promotion Effect on Penaeid Shrimp (the Low Molecular Weight Lignin)

Preparation of Feedstuff

The low molecular weight lignin prepared in Test Example 2 (having a solid content of 1.5% and a content of 7% in terms of catechin with respect to the solid content) was sprayed onto and mixed with a feed mixture (Ebikaniconc made by Bio Science Co., Ltd.) during granulation, at 0.2% on the basis of the weight of the solute and with respect to the dry weight of the feedstuff (0.014% in terms of catechin with respect to the dry weight of the feedstuff, and 0.007 wt % in terms of catechin as the amount of the low molecular weight lignin). The prepared feedstuff was used as a feedstuff containing the low molecular weight lignin.

Evaluation of Growth Promotion Effect

The evaluation was performed in the same manner as in Test Example 11 except that the feedstuff prepared in this Test Example was used. The results are shown in Table 3.

Test Example 13 Growth Promotion Effect on Penaeid Shrimp (the High Molecular Weight Lignin)

Preparation of Feedstuff

The high molecular weight lignin prepared in Test Example 3 and containing diatomaceous earth (having a polyphenol content of 7% in terms of catechin with respect to the solid content) was sprayed onto and mixed with a feed mixture (Ebiconc made by Bio Science Co., Ltd.) during granulation, at 0.2% on the basis of the weight of the solute and with respect to the dry weight of the feedstuff (0.014% in terms of catechin with respect to the dry weight of the feedstuff). The prepared feedstuff was used as a feedstuff containing the high molecular weight lignin.

Evaluation of Growth Promotion Effect

The evaluation was performed in the same manner as in Test Example 11 except that the feedstuff prepared in this Test Example was used. The results are shown in Table 3.

Test Example 14 Growth Promotion Effect on Penaeid Shrimp (Additive-Free)

Preparation of Feedstuff

A feed mixture (Ebiconc made by Bio Science Co., Ltd.) was granulated with nothing added thereto, to prepare an additive-free feedstuff.

Evaluation of Growth Promotion Effect

The evaluation was performed in the same manner as in Test Example 11 except that the additive-free feedstuff in this Test Example was used. The results are shown in Table 3.

Test Example 15 Growth Promotion Effect on Penaeid Shrimp (Bagasse Hydrothermally-Processed Liquid)

Preparation of Feedstuff

The bagasse hydrothermally-processed liquid prepared in Test Example 5 was sprayed onto and mixed with a feed mixture (Ebiconc made by Bio Science Co., Ltd.) during granulation, at 0.2% on the basis of the weight of the solute and with respect to the dry weight of the feedstuff (0.0002% in terms of catechin with respect to the dry weight of the feedstuff).

Evaluation of Growth Promotion Effect

The evaluation was performed in the same manner as in Test Example 11 except that the feedstuff prepared in this Test Example was used. The results are shown in Table 3.

TABLE 3

Growth Promotion Effect on Penaeid Shrimp

| | Number of Shrimp that Survived (shrimp) | Average Body Weight (g) | Average Full Length (mm) |
|---|---|---|---|
| Test Example 11 (Low Molecular Weight Lignin and High Molecular Weight Lignin) | 58 | 0.49 | 39.8 |
| Test Example 12 (Low Molecular Weight Lignin) | 57 | 0.51 | 40.7 |
| Test Example 13 (High Molecular Weight Lignin) | 44 | 0.51 | 39.9 |
| Test Example 14 (Additive-free) | 40 | 0.47 | 39.2 |
| Test Example 15 (Bagasse Hydrothermally-processed Liquid) | 17 | 0.43 | 36.9 |

As shown in Table 3, the result revealed that the number of Penaeid shrimp that survived, the body weight, and the full length of *Amphiprion ocellaris* individuals increased when the feedstuff containing the low molecular weight lignin and the high molecular weight lignin, the feedstuff containing the low molecular weight lignin, and the feedstuff containing the high molecular weight lignin in Test Examples 11 to 13 were used, compared when the additive-free feedstuff in Test Example 14 was used.

Figure 5:
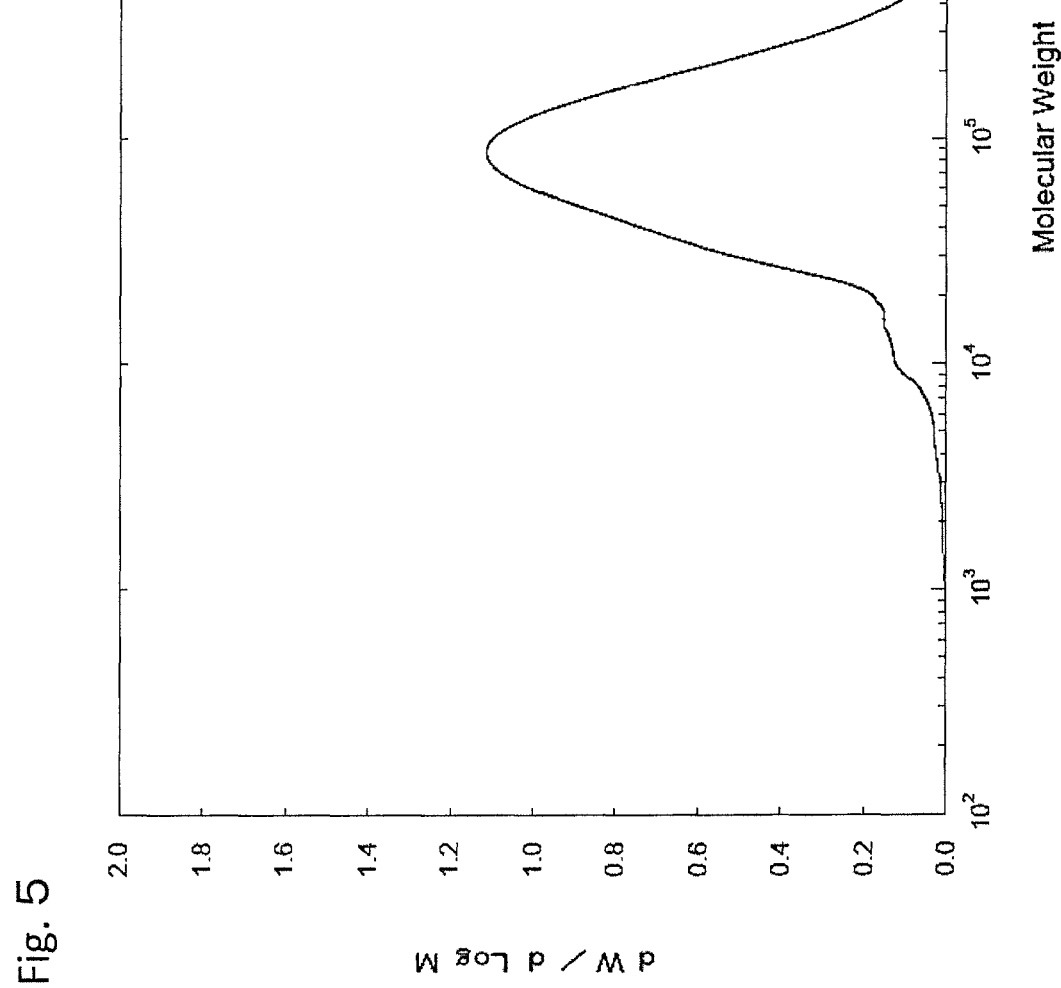
FIG. 5 shows a specific example of the GPC molecular weight analysis result of a lignosulfonic acid liquid.

Reference Example 4 GPC Molecular Weight Analysis of Lignosulfonic Acid Liquid A lignosulfonic acid (a solution of 3% SAN-X P252, made by Nippon Paper Chemicals Co., Ltd., dissolved in an aqueous solution adjusted to pH 10 with NaOH) that is a generally and commercially available lignin product was subjected to GPC molecular weight analysis using the method described in Reference Example 1. The result is shown in FIG. 5. This result confirms that the obtained lignin contained a lignin having a peak at a molecular weight of 100,000, not containing our low molecular weight lignin nor our high molecular weight lignin. In addition, the number average molecular weight was 39,000.

Figure 6:
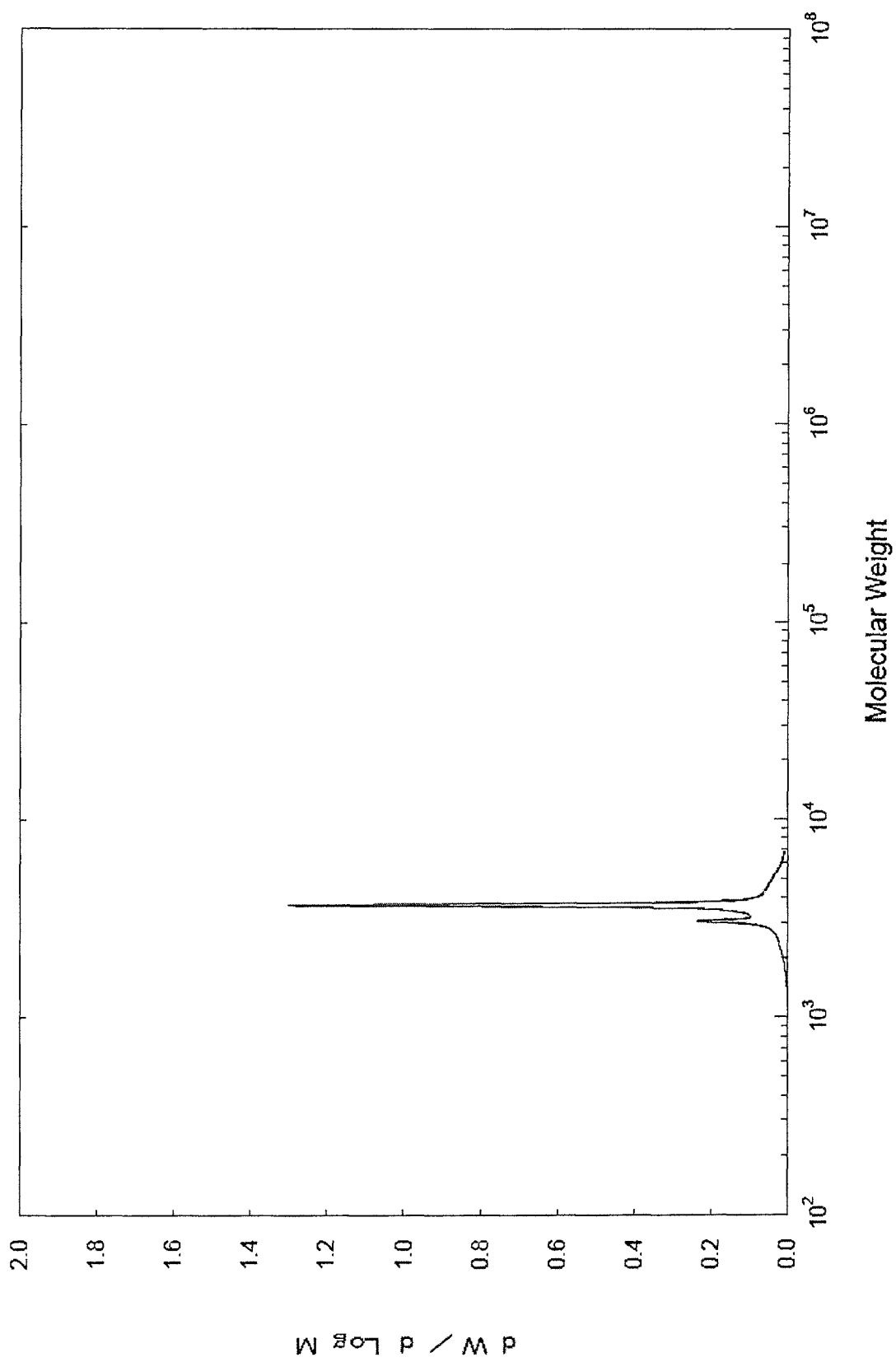
FIG. 6 shows a specific example of the GPC molecular weight analysis result of an alkaline hydrothermally-processed liquid.

Reference Example 5 GPC Molecular Weight Analysis of Lignin Having a Molecular Weight Peak at 4,000 or Less, Wherein the Molecular Weight Peak is Measured at a Wavelength of 254 nm by GPC Molecular Weight Analysis Using an UV Detector Bagasse in an amount of 1 kg (purchased from Taito Nosan K.K., produced in Vietnam) at 5 wt % by dry weight was added to and mixed with a 0.6 (wt/wt) % sodium hydroxide aqueous solution, the resulting mixture was allowed to react at 180° C. for five minutes, and adjusted to pH 7 with 6 N hydrochloric acid, and then, the solid was separated through a sieve, and filtrated through an MF film (tradename: TREFIL HFS Type, made by Toray Industries, Inc.) to prepare a bagasse alkaline hydrothermally-processed liquid. This alkaline hydrothermally-processed liquid was subjected to GPC molecular weight analysis using the method described in Reference Example 1. The analysis result is shown in FIG. 6. This analysis result confirms that the obtained lignin contained a lignin having a peak at a molecular weight of 3,700, not containing the low molecular weight lignin nor the high molecular weight lignin. In addition, the number average molecular weight was 3,300.

The invention claimed is:

1. An aquatic organism growth promotor comprising, as an effective ingredient, at least one of a low molecular weight lignin having a molecular weight peak in a molecular weight range of 4,000 to 9,500 and a high molecular weight lignin having a molecular weight peak in a molecular weight range of 10,000 to 40,000, wherein said molecular weight peak is measured at a wavelength of 254 nm by GPC molecular weight analysis using an UV detector.

2. The aquatic organism growth promotor according to claim 1, wherein said at least one of low molecular weight lignin and said high molecular weight lignin are/is derived from an alkaline hot-water extract from bagasse.

3. The aquatic organism growth promotor according to claim 1, that promotes the ecdysis of a crustacean.

4. An aquatic organism growth promotion feedstuff, comprising the aquatic organism growth promotor according to claim 1.

5. The aquatic organism growth promotion feedstuff according to claim 4, comprising said at least one of low molecular weight lignin and said high molecular weight lignin, wherein the lignin(s) content as a polyphenol amount is 0.007 wt % or more in terms of catechin.

6. A method of promoting aquatic organism growth, comprising administering the aquatic organism growth promotor according to claim 1, to an aquatic organism.

7. A method of promoting aquatic organism growth, comprising feeding the aquatic organism growth promotion feedstuff according to claim 4, to an aquatic organism.

8. The method of promoting aquatic organism growth according to claim 7, wherein said aquatic organism is a crustacean.

9. The aquatic organism growth promotor according to claim 2, that promotes the ecdysis of a crustacean.

10. An aquatic organism growth promotion feedstuff, comprising the aquatic organism growth promotor according to claim 2.

11. The aquatic organism growth promotion feedstuff according to claim 10, comprising said at least one of low molecular weight lignin and said high molecular weight lignin, wherein the lignin(s) content as a polyphenol amount is 0.007 wt % or more in terms of catechin.

12. A method of promoting aquatic organism growth, comprising administering the aquatic organism growth promotor according to claim 2, to an aquatic organism.

13. A method of promoting aquatic organism growth, comprising feeding the aquatic organism growth promotion feedstuff according to claim 5, to an aquatic organism.

14. The method of promoting aquatic organism growth according to claim 7, wherein said aquatic organism is a crustacean.

* * * * *